(12) United States Patent
Kitamura et al.

(10) Patent No.: US 12,109,281 B2
(45) Date of Patent: Oct. 8, 2024

(54) OIL-IN-WATER EMULSIFIED COSMETIC

(71) Applicant: LVMH RECHERCHE, Saint Jean de Braye (FR)

(72) Inventors: Miyako Kitamura, Tokyo (JP); Mai Ozawa, Tokyo (JP); Takayoshi Sakoda, Tokyo (JP)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 16/641,528

(22) PCT Filed: Dec. 18, 2018

(86) PCT No.: PCT/EP2018/085696
§ 371 (c)(1),
(2) Date: Feb. 24, 2020

(87) PCT Pub. No.: WO2019/121817
PCT Pub. Date: Jun. 27, 2019

(65) Prior Publication Data
US 2020/0206097 A1    Jul. 2, 2020

(51) Int. Cl.
*A61K 8/06* (2006.01)
*A61K 8/90* (2006.01)
(Continued)

(52) U.S. Cl.
CPC .............. *A61K 8/062* (2013.01); *A61K 8/90* (2013.01); *A61K 8/92* (2013.01); *A61Q 19/007* (2013.01)

(58) Field of Classification Search
CPC ........ A61Q 19/00; A61Q 17/04; A61Q 11/00; A61Q 5/02; A61Q 5/12; A61Q 19/10; A61Q 5/004; A61Q 5/06; A61Q 19/007; A61Q 5/00; A61Q 5/006; A61Q 9/02; A61Q 9/04; A61Q 15/00; A61Q 1/02; A61Q 13/00; A61Q 19/08; A61Q 1/06; A61Q 1/10; A61Q 1/12; A61Q 1/00; A61Q 1/04; A61Q 1/08; A61Q 17/00; A61Q 19/008; A61Q 19/04; A61Q 5/002; A61K 2300/00; A61K 9/0014; A61K 45/06; A61K 47/10; A61K 47/44; A61K 31/19; A61K 31/23; A61K 47/06; A61K 47/12; A61K 31/231; A61K 31/65; A61K 47/24; A61K 8/31; A61K 9/122; A61K 31/192; A61K 8/342; A61K 31/25; A61K 9/12; A61K 2800/10; A61K 2800/31; A61K 2800/33; A61K 31/137; A61K 31/4164; A61K 31/57; A61K 31/573; A61K 31/593; A61K 47/02; A61K 8/361; A61K 9/0048; A61K 9/124; A61K 47/14; A61K 8/0241; A61K 8/892; A61K 31/20; A61K 47/34; A61K 9/0043; A61K 31/155; A61K 31/075; A61K 2800/48; A61K 8/895; A61K 9/0046; A61K 9/0053; A61K 9/06; A61K 31/00; A61K 31/045; A61K 31/14; A61K 31/215; A61K 47/183; A61K 47/20; A61K 8/375; A61K 8/731; A61K 8/894; A61K 8/922; A61K 2800/412; A61K 31/085; A61K 31/185; A61K 31/191; A61K 31/194; A61K 31/685; A61K 31/785; A61K 33/38; A61K 47/186; A61K 8/37; A61K 8/86; A61K 8/891; A61K 9/007; A61K 9/107; A61K 2800/56; A61K 2800/592; A61K 2800/65; A61K 2800/654; A61K 2800/805; A61K 33/42; A61K 8/11; A61K 8/23; A61K 8/26; A61K 8/345; A61K 8/55; A61K 8/556; A61K 8/732; A61K 8/736; A61K 8/817; A61K 8/84; A61K 8/893; A61K 8/92; A61K 9/0034; A61K 9/1652; A61K 9/5021; A61K 31/255; A61K 31/353; A61K 31/575; A61K 36/13; A61K 36/18; A61K 36/61; A61K 47/38; A61K 8/042; A61K 8/06; A61K 8/062; A61K 8/585; A61K 2039/55566; A61K 2800/591; A61K 2800/624; A61K 2800/651; A61K 2800/652; A61K 31/05; A61K 31/165; A61K 31/22; A61K 31/355; A61K 31/522; A61K 31/59; A61K 31/7056; A61K 39/0008; A61K 39/39; A61K 47/32; A61K 8/022; A61K 8/0233; A61K 8/0279; A61K 8/044; A61K 8/046; A61K 8/064; A61K 8/20; A61K 8/44; A61K 8/738;

(Continued)

(56) References Cited

U.S. PATENT DOCUMENTS

2011/0177143 A1* 7/2011 Tamura .................... A61Q 1/06
424/401

FOREIGN PATENT DOCUMENTS

JP    2015193546    * 11/2015  ............... A61K 8/92
JP    2017031092      2/2017
WO   WO2008/052956 A1 * 5/2008  ............... A61K 8/39

OTHER PUBLICATIONS

Database GNPD Mintel, Jul. 1, 2014, "Primitive Cream", XP002780663, Database accession No. 2551445. (Year: 2014).*

(Continued)

*Primary Examiner* — Audrea B Coniglio
(74) *Attorney, Agent, or Firm* — HSML P.C.

(57) ABSTRACT

An oil-in-water emulsified cosmetic comprising an aqueous medium, an alkali-soluble polymer having a carboxy group and an amphiphilic side chain comprising a hydrophobic block and a hydrophilic block and bonded to the main chain at the hydrophilic block end, a nonionic surfactant having a
(Continued)

C3-C6 straight-chain or cyclic polyol residue and an HLB of (6.0-12.0), a liquid oil and a paste oil.

4 Claims, No Drawings

(51) Int. Cl.
*A61K 8/92* (2006.01)
*A61Q 19/00* (2006.01)

(58) Field of Classification Search
CPC ........ A61K 8/89; A61K 8/897; A61K 9/0095; A61K 9/10; A61K 9/1075; A61K 9/48; A61K 2039/505; A61K 2800/262; A61K 2800/596; A61K 31/44; A61K 31/445; A61K 38/16; A61K 47/08; A61K 47/18; A61K 47/22; A61K 47/26; A61K 47/46; A61K 8/0295; A61K 8/19; A61K 8/27; A61K 8/29; A61K 8/34; A61K 8/35; A61K 8/365; A61K 8/39; A61K 8/42; A61K 8/442; A61K 8/553; A61K 8/60; A61K 8/64; A61K 8/678; A61K 8/81; A61K 8/8152; A61K 8/8158; A61K 8/90; A61K 8/9789; A61K 8/9794; A61K 9/14; A61K 9/703; A61K 31/7072; A61K 2800/40; A61K 31/166; A61K 31/366; A61K 31/381; A61K 31/404; A61K 31/41; A61K 31/426; A61K 31/47; A61K 8/0229; A61K 8/25; A61K 2800/621; A61K 8/0216; A61K 8/0254; A61K 8/85; A61P 31/04; A61P 17/00; A61P 31/00; A61P 31/10; A61P 31/12; A61P 17/02; A61P 11/00; A61P 29/00; A61P 15/00; A61P 1/00; A61P 17/10; A61P 17/12; A61P 17/16; A61P 25/24; A61P 27/16; A61P 33/00; A61P 37/08; A61P 9/00; A61P 25/00; A61P 27/02; A61P 31/02; A61P 37/06; A61P 15/02; A61P 17/04; A61P 17/06; A61P 17/08; A61P 17/14; A61P 19/02; A61P 23/00; A61P 25/20; A61P 27/06; A61P 31/14; A61P 31/18; A61P 31/20; A61P 31/22; A61P 33/10; A61P 33/14; A61P 35/00; A61P 37/00; A61P 37/02; A61P 37/04; A61P 39/06; A61P 5/00; A61P 7/10; A61P 9/08; A61P 11/02; A61P 43/00; A61P 11/04; A61P 3/02; A61P 3/06; A61P 41/00; A61P 25/02; A61P 25/04; A61P 39/00; A61P 21/00; A61P 9/10; A61P 1/08; A61P 1/16; A61P 11/14; A61P 5/38; A61P 9/04; A61P 35/02

See application file for complete search history.

(56) References Cited

OTHER PUBLICATIONS

Database GNPD [Online] Mintel, "Primitive Cream," XP002780663, Database accession No. 2551445, Jul. 1, 2014, 5 pages.
Database GNPD [Online] Mintel, "Spray Nutrition Body Lotion," XP055566964, retrieved from www.gnpd.com, Database accession No. 5587401, Apr. 11, 2018, 2 pages.
International Search Report and Written Opinion issued for International Patent Application No. PCT/EP2018/085696, Date of mailing: Mar. 20, 2019, 13 pages.

* cited by examiner

OIL-IN-WATER EMULSIFIED COSMETIC

BACKGROUND OF THE INVENTION

Field of the Invention

The present invention relates to an oil-in-water emulsified cosmetic.

Related Background Art

Oil-in-water emulsions are cosmetics capable of moisturizing the skin, while maintaining a watery light sensation, to a greater degree than solubilized transparent formulations that contain essentially no oil components, and for this reason they are used in a wide variety of skin care products.

An oil-in-water emulsion generally comprises an aqueous component, an oil component and a surfactant for emulsification of the oil component, the aqueous component usually containing components such as polyols and polysaccharides (see PTL 1, for example).

CITATION LIST

Patent Literature

[PTL 1] Japanese Unexamined Patent Application Publication No. 2017-31092

SUMMARY OF THE INVENTION

In the aqueous component, it is common to include synthetic water-soluble polymers, buffers and water-soluble actives in addition to polyols or polysaccharides, as they can provide a moisturizing effect, but the present inventors have found that such components also cause the cosmetic to have a heavier, stickier texture, even when added in small amounts.

This problem with formulating such cosmetics has presented a technical obstacle against development of oil-in-water emulsified cosmetics with freshness and moisturizing effects and less stickiness, and consequently such products have not yet been marketed.

It is an object of the present invention to provide an oil-in-water emulsified cosmetic having a watery light sensation without stickiness, and yet still capable of exhibiting a long lasting moisturizing effect.

The invention provides an oil-in-water emulsified cosmetic comprising (A) an aqueous medium, (B) an alkali-soluble polymer having a carboxy group and an amphiphilic side chain comprising a hydrophobic block and a hydrophilic block and bonded to the main chain on the hydrophilic block end, (C) a nonionic surfactant having at least one C3-6 straight-chain or cyclic polyol residue and an HLB of 6-12.0, (D) a liquid oil and (E) a paste oil, wherein the mass ratio of the paste oil (E) with respect to the liquid oil (D) is greater than 0 and no greater than 1, with the proviso that the oil-in-water emulsified cosmetic comprises no silicone-based oil component.

The "aqueous medium (A)" will hereunder also be referred to simply as "component (A)", and the other components will be referred to similarly.

The hydrophilic block can be bonded to the hydrophobic block.

The oil-in-water emulsified cosmetic of the invention exhibits a satisfactory feel during use due to its excellent freshness and stickiness free, while its long lasting moisturizing effect. The emulsified cosmetic containing no silicone-based oil component additionally prevents a slippery feeling. The emulsified state is also stable over extended periods of time. The vast majority of consumers have high demands for the moisturizing effects of skin care products while also desiring watery light sensation, and the oil-in-water emulsified cosmetic of the invention meets these demands.

Component (B), which has a hydrophilic block on a side chain and also includes a carboxy group, facilitates swelling, dispersion or dissolution in water, exhibiting satisfactory water solubility under neutral to alkaline conditions.

On the other hand, component (B) also has a hydrophobic block at the side chain end, and therefore its hydrophobic portions associate with the hydrophobic groups of the nonionic surfactant (C3-C6 straight-chain or cyclic polyol residues), to form an associated complex in component (A). The oil-in-water emulsified cosmetic of the invention produces a light sensation without stickiness, the effect being due to the combination between the associative polymers (component (B)) and component (C).

Component (B) is an associative water-soluble polymer that not only imparts viscosity to the oil-in-water emulsified cosmetic but also has emulsifying ability for the oil agent, and when it is added alone to a cosmetic to impart viscosity and emulsifying ability, it produces stickiness on the skin similar to when other water-soluble polymers are used. According to the present invention, however, component (B) and component (C) produce an associated complex so that high emulsifying ability can be exhibited even with a lower amount of (B) added, and stickiness is not produced as a result.

The oil-in-water emulsified cosmetic of the invention also comprises an oil agent which is a combination of component (D) and component (E), and exhibits a long lasting moisturizing effect. Addition of the oil agent increases the viscosity while presumably causing formation of associated complexes, so that the moisturizing effect is enhanced and the stability of the cosmetic is also increased.

The oil agent in an oil-in-water emulsified cosmetic provides a moisturizing effect without causing stickiness, but it is a difficult to stably emulsify and disperse the oil agent in an aqueous medium. Common solutions to this problem are to add excess amounts of surfactant, or to use co-surfactant and water-soluble thickener. Such formulations stabilize the cosmetics, but still produce an undesirable feeling of heaviness and stickiness.

The oil-in-water emulsified cosmetic of the invention, however, does not require addition of excess surfactants, and can provide sufficiently high stability for the emulsion without addition of other components to increase the emulsified stability.

The alkali-soluble polymer may comprise an alkoxycarbonyl group, and an amphiphilic side chain with a C12 to C24 hydrocarbon skeleton as the hydrophobic block and a polyoxyethylene skeleton as the hydrophilic block. The nonionic surfactant may have a glycerin residue, sorbitol residue or sucrose residue, and its HLB may be 6.0-12.0.

Using the respective structures described above for component (B) and component (C) will increase their ability to form an associated complex and result in a superior effect of the invention, that is, providing freshness, preventing stickiness and imparting moisture, while greater emulsified stability will also be exhibited.

The mass ratio of the paste oil with respect to the liquid oil may be greater than 0 and no greater than 1.

The paste oil exhibits a greater effect of moisturizing and reducing stickiness compared to a liquid oil, but from the viewpoint of stability of the emulsion it may not be desirable for it to be added in an excessive amount. When the mass ratio of the paste oil is within the so range specified above, the oil-in-water emulsified cosmetic of the invention exhibits very satisfactory stability.

Either or both the liquid oil and the paste oil may be polar oil agents. That is, a polar liquid oil and/or a polar paste oil may be used. The moisturizing effect will be even more prolonged by using such oil agents.

According to the present invention there is provided an oil-in-water emulsified cosmetic having a watery light sensation without stickiness, and yet still capable of exhibiting an adequate long lasting moisturizing effect.

DESCRIPTION OF EMBODIMENTS

Embodiments of the invention will now be described, with the understanding that they are not intended to be restrictive on the invention.

Component (A) in the oil-in-water emulsified cosmetic of this embodiment is an aqueous medium which contains at least water, as the medium for components (B) to (E). Component (A) may consist of water alone or it may comprise other water-soluble components in water.

Water-soluble components include polyols, monoalcohols, polysaccharides, nonionic surfactants other than component (C), anionic surfactants, cationic surfactants, amphoteric surfactants, buffers, preservatives, synthetic water-soluble polymers, ultraviolet absorbers, ultraviolet scatterings, antimicrobial agents, anti-inflammatory agents, perfumes, antioxidants, pH regulators, chelating agents, vitamins, amino acids and plant extracts.

Examples of polyols include butylene glycol, pentylene glycol and glycerin, and examples of polysaccharides include sulfated polysaccharides. Nonionic surfactants that may be used (other than component (C)) include ethylene oxide addition products of sorbitan fatty acid esters such as polysorbate 20 (HLB:16.7), polysorbate 60 (HLB:14.9) and polysorbate 80 (HLB:15), and sorbitan fatty acid esters such as sorbitan sesquioleate (HLB:5).

Sodium phosphate, disodium phosphate and disodium EDTA are typical buffers that may be used, phenoxyethanol is a typical preservative, and ethanol is a typical monoalcohol.

Component (B) in the oil-in-water emulsified cosmetic is an alkali-soluble polymer comprising a carboxy group, an amphiphilic side chain comprising a hydrophobic block and a hydrophilic block and bonded to the main chain on the hydrophilic block end.

That is, component (B) has at least a carboxy group and an amphiphilic side chain, the amphiphilic side chain including a hydrophobic block and a hydrophilic block and being bonded to the main chain on the hydrophilic block end.

A hydrophobic block is one that has a length of more than one carbon atom and is itself hydrophobic, and typically it is a hydrocarbon skeleton. A hydrophobic block is preferably a hydrocarbon skeleton of 12 to 24 carbon atoms; and more preferably it is a C12 to C24 alkyl group. Such alkyl groups include dodecyl (lauryl), tridecyl, tetradecyl, pentadecyl, hexadecyl, heptadecyl, octadecyl, nonadecyl, eicosyl and docosyl (behenyl) groups. The alkyl group preferably has an even number of carbons, and is preferably a dodecyl, octadecyl or docosyl group.

A hydrophilic block is one that has a length of more than one carbon atom and is itself hydrophilic, and typically it is a polyoxyalkylene skeleton. The hydrophilic block is preferably composed of a polyoxyethylene skeleton, which may have 10 to 30 oxyethylene repeating units. That is, the hydrophilic block preferably has a —($CH_2CH_2O$)n- skeleton, where n is 10 to 30, more preferably 12 to 25 and even more preferably 20 to 25. The hydrophilic block may be directly bonded to the main chain, or bonded via a linker. The linker may be an oxycarbonyl group (—CO—O—), the —O— portion preferably being bonded to a carbon atom of the polyoxyalkylene skeleton.

Component (B) may have an alkoxycarbonyl group, the alkyl group of the alkoxycarbonyl group preferably being a C1-C24 alkyl group. Such alkyl groups include methyl, ethyl, butyl, hexyl, octyl, decyl, dodecyl (lauryl), tetradecyl, hexadecyl, octadecyl, eicosyl and docosyl (behenyl) groups.

Component (B) is preferably a polymer comprising an ethylenic unsaturated compound with a carboxy group and an ethylenic unsaturated compound with the abovementioned amphiphilic group as repeating units, while it may also have an ethylenic unsaturated compound with the abovementioned alkoxycarbonyl group as an additional repeating unit. A more preferred polymer is one comprising (meth)acrylic acid, alkyl (meth)acrylate ester and (meth) acrylic acid polyoxyethylene monoalkyl ether ester as repeating units [That is (meth)acrylic acid/alkyl (meth) acrylate/(meth)acrylic acid-POE-monoalkyl ether ester copolymer).]. The term "(meth)acrylic" refers to acrylic or methacrylic, which likewise applies to other analogs such as (meth)acryloyl.

Component (B) is an alkaline-soluble water-soluble polymer, which not only imparts viscosity to the cosmetic but also has emulsifying ability for the oil agent. Specifically, it can be used to disperse in the aqueous medium of the formulation, and neutralized with a base such as sodium hydroxide. It may also be referred to as a hydrophobically-modified alkali soluble polymer. Examples for component (B) are Aculyn™ 22 and Aculyn™ 28, by Dow Chemical Corp.

A drastic increase in viscosity is produced by component (B) in combination with component (C). This phenomenon occurs because the hydrophobic residues (such as alkyl groups) of component (B) and the component (C) interact together in the oil-in-water emulsified cosmetic, forming associated complexes. The associated complexes formed even by the small amount of component (B) and component (C) produce a characteristic sensation when applied to the skin, as they are immediately converted from gel to liquid form.

Component (C) in the oil-in-water emulsified cosmetic is a nonionic surfactant having at least one C3-C6 straight-chain or cyclic polyol residue, and having an HLB of 6.0-12.0. Component (C), in other words, comprises at least one C3-C6 straight-chain polyol residue or C3-C6 cyclic polyol residue, and its HLB is in the range specified above. When HLB is less than 6.0, solubility into the aqueous medium declines and emulsified stability is reduced. Furthermore, it is impossible to obtain the effect achieved by the present invention (a watery light sensation without stickiness, and an adequate long lasting moisturizing effect). Conversely, when HLB exceeds 12.0, freshness, and emulsified stability deteriorate, and the abovementioned effect cannot be obtained.

The HLB is the Hydrophile-Lipophile Balance commonly used in the field of surfactants, and it can be calculated by a conventional formula such as the following published by Oda and Teramura:

$$HLB=(\Sigma Inorganic\ value)\times 10/(\Sigma organic\ value)$$

When the nonionic surfactant is a commercial product, the HLB value listed in the product catalog may be used.

Glycerin residue is an example of a C3 straight-chain polyol residue, and sorbitol residue is an example of a C6 straight-chain polyol residue. Sucrose residue is one having two C6 cyclic polyol residues.

Component (C) may be a fatty ester of an oxyethylene addition product of a C3-C6 straight-chain or cyclic polyol. The fatty acid may be used singly or in combination of two or more kinds thereof. The alkyl portion in the fatty acid may be a C6-C24 alkyl group, examples of which include hexyl, octyl, decyl, dodecyl (lauryl), tridecyl, tetradecyl, pentadecyl, hexadecyl, heptadecyl, octadecyl, nonadecyl, eicosyl and docosyl (behenyl) groups. An example of component (C) of such a type is polyoxyethylene(20) glyceryl triisostearate (for example, PEG-20 glyceryl triisostearate).

Alternatively, component (C) may be a fatty acid ester of an oxyethylene addition product of a C3-C6 straight-chain or cyclic polyol. Examples for component (C) of this type also include polyoxyethylene hydrogenated castor oil and sorbitol oxyethylene addition product fatty acid ester. PEG-10 hydrogenated castor oil can be given as an example of this polyoxyethylene hydrogenated castor oil. Furthermore, sorbitol oxyethylene addition product oleic acid ester (sorbeth-6 tetraoleate, sorbeth-30 tetraoleate, etc.) can be given as an example of sorbitol oxyethylene addition product fatty acid ester.

The HLB of component (C) is preferably 7.0-12.0 and more preferably 8.0-12.0. When component (C) has an HLB within this medium range, a satisfactory interaction between the hydrophobic residues of component (B) and component (C) is obtained, and therefore the oil-in-water emulsified cosmetic exhibits a watery light sensation without stickiness.

Component (D) and component (E) in the oil-in-water emulsified cosmetic are oil agents, and specifically a liquid oil and a paste oil, respectively. Any paste oil may be used without any particular restrictions, so long as it is in the form of a paste at 25° C. and can be used in cosmetics, but it is preferred to use an ester oil and/or hydrocarbon oil having a viscosity of 10,000 mPa·s or greater at 25° C., as measured with a Brookfield rotating viscometer. A liquid oil is one having a viscosity of less than 10,000 mPa·s under the same conditions. If the viscosity is excessively high, it may be judged as a paste oil if the consistency at 30° C. (based on JIS-K-2220) is greater than 150.

Adding such oil agents will promote formation of associated complexes that synergistically increase the viscosity, and will result in an oil-in-water emulsified cosmetic that maintains its stability. The oil-in-water emulsified cosmetic exhibits a watery light sensation without stickiness, and maintains a long lasting moisturizing effect. Common oil agents, with the exception of silicone-based oil components, have the property of more easily penetrating stratum corneum of skin compared to water-soluble components, and can thus impart a greater moisturizing effect, but it tends to be more difficult to ensure the stability of an oil-in-water emulsified cosmetic than that of a formulation containing no oil agent. According to the invention, however, the effect described above is obtained due to formation of the associated complexes, and combining a liquid oil and a paste oil makes it possible to increase the moisturizing effect while further reducing stickiness.

Liquid oils include isononyl isononanoate, isotridecyl isononanoate, ethylhexyl palmitate, cetyl ethylhexanoate, neopentylglycol diethylhexanoate, neopentylglycol dicaprate, triethylhexanoin, glyceryl tri(caprylate/caprate), triisostearin, trimethylolpropane triisostearate, pentaerythrityl tetraethylhexanoate, pentaerythrityl tetraisostearate, polyglyceryl-2 tetraisostearate, propanediol di(caprylate/caprate), propanediol diisostearate and polyglyceryl-6 octacaprylate.

Other liquid oils include octyldodecyl lactate, diisostearyl malate, polyglyceryl-2 isostearate, polyglyceryl-2 diisostearate, polyglyceryl-2 triisostearate, ditrimethylolpropane (isostearate/sebacate) oligoester, erythrityl triethylhexanoate, dipentaerythrityl tripolyhydroxystearate, isostearic acid trehalose esters, dipentaerythrityl pentaisostearate, ethylhexyl hydroxystearate, polyhydroxystearic acid, liquid paraffin, squalane, α-olefin oligomer, isododecane and isohexadecane.

Paste oils include vegetable oil pastes, shea butter (*Butyrospermum parkii*), mango seed butter (*Mangifera indica*) and avocado butter (*Persea gratissima*), cholesteryl hydroxystearate, phytostearyl hydroxystearate, phytostearyl oleate, dipentaerythrityl hexa(hydroxystearate/stearate/rosinate), dipentaerythrityl tetra(hydroxystearate/isostearate), dipentaerythrityl hexahydroxy stearate, glyceryl (ethylhexanoate/stearate/adipate), glyceryl tri(caprylate/caprate/myristate/stearate), hydrogenated palm oil, vaseline and dipentaerythrityl hexa(behenate/benzoate/ethylhexanoate).

Polar oils are preferred over non-polar oils for both liquid oils and paste oils, from the viewpoint of persistence of the moisturizing effect. Preferred polar liquid oils include isononyl isononanoate and ethylhexyl palmitate, and preferred polar paste oils include vegetable oil pastes, and especially vegetable oil, shea butter, mango seed butter and avocado butter.

The mass ratio of the paste oil with respect to the liquid oil is preferably greater than 0 and no greater than 1, with more preferred ranges being 0.1 to 0.8 and especially 0.2 to 0.5. When the mass ratio of the oil paste is within this range, it is possible to impart very satisfactory stability to the oil-in-water emulsified cosmetic.

The component (B) content is preferably 0.05 to 2.0 mass %, the component (C) content is preferably 0.05 to 5.00 mass %, and the total content of components (D) and (E) is preferably 1 to 40 mass %. Component (A) will constitute the remaining content. These contents are based on the total mass of the oil-in-water emulsified cosmetic.

The viscosity of the oil-in-water emulsified cosmetic at 25° C. is preferably 1000 mPa·s or greater. The viscosity is more preferably 1000 to 10,000 mPa·s and even more preferably 1000 to 5000 mPa·s. A viscosity in this range will improve the stability of the oil-in-water emulsified cosmetic and give it an excellent feel during use.

The oil-in-water emulsified cosmetic can be obtained by mixing and stirring component (A), component (B), component (C), component (D) and component (E), or by mixing and neutralizing component (B) in component (A) and then adding and stirring in component (C), component (D) and component (E).

Examples

The invention will now be illustrated by examples, with the understanding that the invention is not meant to be limited to these examples.

Using the compositions listed in Tables 1 to 3, the aqueous medium (column "A"), oil agent (column "B"), nonionic surfactant (column "C"), co-surfactants, and polymer component (column "D") were mixed and stirred to prepare oil-in-water emulsified cosmetics for Examples 1 to 6 and Comparative Examples 1 to 12. For formulation, the polymer component was mixed and neutralized in the aqueous medium, and a mixture of the oil agent and nonionic surfactant was added and mixed with the solution to obtain an oil-in-water emulsified cosmetic. The contents (mass %) of each of the materials were as shown in Tables 1 to 3.

<Organoleptic Evaluation>

The moisturizing effect persistence, freshness and stickiness free of the oil-in-water emulsified cosmetics of Examples and Comparative Examples were evaluated in a single-use test on skin, by an expert cosmetic evaluation panel from an organization to which the present inventors belong, the evaluation being made on the following scale.

(1) Moisturizing Effect Persistence and Freshness
A: Strong
B: Moderate
C: Almost none
D: None (2) Stickiness Free
A: Absolutely no stickiness
B: Almost no stickiness
C: Slight stickiness
D: Stickiness <Emulsified Stability Evaluation>

The emulsified stabilities of the oil-in-water emulsified cosmetics of Examples and Comparative Examples were evaluated. Each cosmetic was filled into a transparent container and sealed with a cap, and then stored for 1 month at 50° C. Any separation between the oil phase and aqueous phase after storage was observed. The degree of oil phase and aqueous phase separation after storage was evaluated on a 4-level scale of A to D, from low separation to high separation. The results are shown in Table 1.

TABLE 1

| | | Example 1 | Example 2 | Example 3 | Example 4 | Example 5 |
|---|---|---|---|---|---|---|
| A (Aqueous medium) | Butylene glycol | 5 | 5 | 5 | 5 | 5 |
| | Pentylene glycol | 5 | 5 | 5 | 5 | 5 |
| | Glycerin | 5 | 5 | 5 | 5 | 5 |
| | Phenoxyethanol | 0.5 | 0.5 | 0.5 | 0.5 | 0.5 |
| | Sodium phosphate | 0.01 | 0.01 | 0.01 | 0.01 | 0.01 |
| | Disodium phosphate | 0.01 | 0.01 | 0.01 | 0.01 | 0.01 |
| | Disodium EDTA | 0.01 | 0.01 | 0.01 | 0.01 | 0.01 |
| | Ethanol | 5 | 5 | 5 | 5 | 5 |
| | Perfume | 0.1 | 0.1 | 0.1 | 0.1 | 0.1 |
| | Water | rem | rem | rem | rem | rem |
| B (Oil) | Isononyl isononanoate (liquid) | 4 | 2.5 | 4 | 4 | 4 |
| | Vegetable oil (paste) | 1 | 2.5 | 1 | 1 | 1 |
| | Dimethylpolysiloxane (liquid) | — | — | — | — | — |
| C (Surfactant) | PEG-20 glyceryl triisostearate (HLB 8.0) | 1 | 1 | — | — | — |
| | PEG-10 hydrogenated castor oil (HLB 6.5) | — | — | 1 | — | — |
| | SORBETH-6 tetraoleate (HLB 8.5) | — | — | — | — | 1 |
| | SORBETH-30 tetraoleate (HLB 12.0) | — | — | — | 1 | — |
| | PEG-60 hydrogenated castor oil (HLB 14.0) | — | — | — | — | — |
| | PEG-7 glyceryl cocoate (HLB 14.0) | — | — | — | — | — |
| | SORBETH-40 tetraoleate (HLB 12.5) | — | — | — | — | — |
| | Di(C12-15) PARETH-10 phosphate | — | — | — | — | — |
| Co-Surfactants | Sorbitan sesquioleate | 0.1 | 0.1 | 0.1 | 0.1 | 0.1 |
| | Polysorbate 80 | 0.1 | 0.1 | 0.1 | 0.1 | 0.1 |
| D (Polymer component) | Acrylate/Beheneth-25 methacrylate copolymer (solid content: 20%, ACULYN 28) | 2 | 2 | 2 | 2 | 2 |
| | (Acrylate/alkyl acrylate (C10-30)) crosspolymer | — | — | — | — | — |
| | PPG-12/methylenediphenyldiisocyanate) copolymer (EXPERTGEL EG412) | — | — | — | — | — |
| | (PEG-240/decyltetradeceth-20/HDI) copolymer, (ADEKANOL GT-700) | — | — | — | — | — |
| | Sodium hydroxide | sq. | sq. | sq. | sq. | sq. |
| | Total amount (mass %) | 100 | 100 | 100 | 100 | 100 |
| Organo evaluation | Long lasting moisturizing effect | A | B | A | A | A |
| | Freshness | A | B | B | A | B |
| | Stickiness free | A | B | A | B | B |
| | Emulsified stability evaluation | A | B | B | B | B |

TABLE 2

| | | Comp. Example 1 | Comp. Example 2 | Comp. Example 3 | Comp. Example 4 | Comp. Example 5 | Comp. Example 6 | Comp. Example 7 |
|---|---|---|---|---|---|---|---|---|
| A (Aqueous medium) | Butylene glycol | 5 | 5 | 5 | 5 | 5 | 5 | 5 |
| | Pentylene glycol | 5 | 5 | 5 | 5 | 5 | 5 | 5 |
| | Glycerin | 5 | 5 | 5 | 5 | 5 | 5 | 5 |
| | Phenoxyethanol | 0.5 | 0.5 | 0.5 | 0.5 | 0.5 | 0.5 | 0.5 |
| | Sodium phosphate | 0.01 | 0.01 | 0.01 | 0.01 | 0.01 | 0.01 | 0.01 |
| | Disodium phosphate | 0.01 | 0.01 | 0.01 | 0.01 | 0.01 | 0.01 | 0.01 |
| | Disodium EDTA | 0.01 | 0.01 | 0.01 | 0.01 | 0.01 | 0.01 | 0.01 |
| | Ethanol | 5 | 5 | 5 | 5 | 5 | 5 | 5 |
| | Perfume | 0.1 | 0.1 | 0.1 | 0.1 | 0.1 | 0.1 | 0.1 |
| | Water | rem | rem | rem | rem | rem | rem | rem |

TABLE 2-continued

|  |  | Comp. Example 1 | Comp. Example 2 | Comp. Example 3 | Comp. Example 4 | Comp. Example 5 | Comp. Example 6 | Comp. Example 7 |
|---|---|---|---|---|---|---|---|---|
| B (Oil) | Isononyl isononanoate (liquid) | 4 | 4 | 4 | 4 | 4 | 4 | 4 |
|  | Vegetable oil (paste) | 1 | 1 | 1 | 1 | 1 | 1 | 1 |
|  | Dimethylpolysiloxane (Liquid) | — | — | — | — | — | — | — |
| C (Surfactant) | PEG-20 glyceryl triisostearate (HLB 8.0) | 1 | 1 | 1 | — | — | — | — |
|  | PEG-10 hydrogenated castor oil (HLB 6.5) | — | — | — | — | — | — | — |
|  | SORBETH-6 tetraoleate (HLB 8.5) | — | — | — | — | — | — | — |
|  | SORBETH-30 tetraoleate (HLB 12.0) | — | — | — | — | — | — | — |
|  | PEG-60 hydrogenated castor oil (HLB 14.0) | — | — | — | — | 1 | — | — |
|  | PEG-7 glyceryl cocoate (HLB 14.0) | — | — | — | — | — | 1 | — |
|  | SORBETH-40 tetraoleate (HLB 12.5) | — | — | — | — | — | — | 1 |
|  | Di(C12-15) PARETH-10 phosphate | — | — | — | — | — | — | — |
| Co-Surfactant | Sorbitan sesquioleate | 0.1 | 0.1 | 0.1 | 0.1 | 0.1 | 0.1 | 0.1 |
|  | Polysorbate 80 | 0.1 | 0.1 | 0.1 | 0.1 | 0.1 | 0.1 | 0.1 |
| D (Polymer component) | Acrylate/Beheneth-25 methacrylate copolymer Solid content: 20%. ACULYN 28) | — | — | — | 2 | 2 | 2 | 2 |
|  | (Acrylate/alkyl acrylate (C10-30)) crosspolymer | 0.4 | — | — | — | — | — | — |
|  | PPG-12/methylenediphenyl diisocyanate) copolymer (EXPERTGEL EG412) | — | 0.4 | — | — | — | — | — |
|  | (PEG-240/decyltetradeceth-20/HDI) copolymer, (ADEKANOL GT-700) | — | — | 0.4 | — | — | — | — |
|  | Sodium hydroxide | s.q. | s.q. | s.q. | s.q. | s.q. | s.q. | s.q. |
|  | Total amount (mass %) | 100 | 100 | 100 | 100 | 100 | 100 | 100 |
| Organo evaluation | Long lasting moisturizing effect | B | B | B | B | B | B | B |
|  | Freshness | C | D | D | D | C | C | C |
|  | Stickiness free | D | C | C | B | C | C | C |
|  | Emulsified stability evaluation | C | D | D | C | D | D | D |

TABLE 3

|  |  | Comp. Example 8 | Comp. Example 9 | Comp. Example 10 | Comp. Example 11 | Comp. Example 12 |
|---|---|---|---|---|---|---|
| A (Aqueous medium) | Butylene glycol | 5 | 5 | 5 | 5 | 5 |
|  | Pentylene glycol | 5 | 5 | 5 | 5 | 5 |
|  | Glycerin | 5 | 5 | 5 | 5 | 5 |
|  | Phenoxyethanol | 0.5 | 0.5 | 0.5 | 0.5 | 0.5 |
|  | Sodium phosphate | 0.01 | 0.01 | 0.01 | 0.01 | 0.01 |
|  | Disodium phosphate | 0.01 | 0.01 | 0.01 | 0.01 | 0.01 |
|  | Disodium EDTA | 0.01 | 0.01 | 0.01 | 0.01 | 0.01 |
|  | Ethanol | 5 | 5 | 5 | 5 | 5 |
|  | Perfume | 0.1 | 0.1 | 0.1 | 0.1 | 0.1 |
|  | Water | rem | rem | rem | rem | rem |
| B (Oil) | Isononyl isononanoate (liquid) | 4 | 5 | — | — | — |
|  | Vegetable oil (paste) | 1 | — | 5 | — | — |
|  | Dimethylpolysiloxane (liquid) | — | — | — | — | 5 |
| C (Surfactant) | PEG-20 glyceryl triisostearate (HLB 8.0) | — | 1 | 1 | — | 1 |
|  | PEG-10 hydrogenated castor oil (HLB 6.5) | — | — | — | — | — |
|  | SORBETH-6 tetraoleate (HLB 8.5) | — | — | — | — | — |
|  | SORBETH-30 tetraoleate (HLB 12.0) | — | — | — | — | — |
|  | PEG-60 hydrogenated castor oil (HLB 14.0) | — | — | — | — | — |
|  | PEG-7 glyceryl cocoate (HLB 14.0) | — | — | — | — | — |
|  | SORBETH-40 tetraoleate (HLB 12.5) | — | — | — | — | — |
|  | Di(C12-15) PARETH-10 phosphate | 1 | — | — | — | — |
| Co-Surfactant | Sorbitan sesquioleate | 0.1 | 0.1 | 0.1 | 0.1 | 0.1 |
|  | Polysorbate 80 | 0.1 | 0.1 | 0.1 | 0.1 | 0.1 |
| D (Polymer component) | Acrylate/Beheneth-25 methacrylate copolymer (solid content: 20%. ACULYN 28) | 2 | 2 | 2 | 2 | 2 |
|  | (Acrylate/alkyl acrylate (C10-30)) crosspolymer | — | — | — | — | — |
|  | PPG-12/methylenediphenyl diisocyanate) copolymer (EXPERTGEL EG412) | — | — | — | — | — |
|  | (PEG-240/decyltetradeceth-20/HDI) copolymer, (ADEKANOL GT-700) | — | — | — | — | — |
|  | Sodium hydroxide | s.q. | s.q. | s.q. | s.q. | s.q. |
|  | Total amount (mass %) | 100 | 100 | 100 | 100 | 100 |
| Organo evaluation | Long lasting moisturizing effect | B | B | B | D | D |
|  | Freshness | C | B | B | C | B |
|  | Stickiness free | C | C | B | D | B |
|  | Emulsified stability evaluation | D | B | D | B | B |

What is claimed is:

1. An oil-in-water emulsified cosmetic comprising:
   (A) an aqueous medium,
   (B) an alkali-soluble polymer having a carboxy group and an amphiphilic side chain comprising a hydrophobic block and a hydrophilic block and being bonded to the main chain at the hydrophilic block end,
   (C) PEG-20 glyceryl triisostearate as a nonionic surfactant having an HLB of 6.0-12.0,
   (D) a liquid oil having a viscosity of less than 10,000 mPa·s at 25° C., as measured with a Brookfield rotating viscometer, and
   (E) a paste oil having a viscosity of 10,000 mPa·s or greater at 25° C., as measured with a Brookfield rotating viscometer or a paste oil having a consistency of greater than 150 at 30° C. based on JIS-K-2220,
   wherein the mass ratio of the paste oil (E) with respect to the liquid oil (D) is in a range from 0.2 to 0.5, with the proviso that the oil-in-water emulsified cosmetic comprises no silicone-based oil component.

2. The oil-in-water emulsified cosmetic according to claim 1, wherein the alkali-soluble polymer further comprises alkoxycarbonyl group, and the amphiphilic side chain comprises a C12 to C24 hydrocarbon skeleton as the hydrophobic block and a polyoxyethylene skeleton as the hydrophilic block.

3. The oil-in-water emulsified cosmetic according to claim 1, wherein either or both the liquid oil and the paste oil are polar oil agents.

4. The oil-in-water emulsified cosmetic according to claim 1, wherein the component (C) content is in a range from 0.05 to 5.00 mass %.

* * * * *